United States Patent [19]
Kawamura et al.

[11] 4,022,664
[45] May 10, 1977

[54] PROCESS FOR BIOCHEMICAL OPTICAL RESOLUTION OF ALPHA-TOCOPHERAL

[75] Inventors: Tamio Kawamura, Inuyama; Satoru Kato; Yasunori Ikeda, both of Ichinomiya; Noriaki Kuwana, Inuyama, all of Japan

[73] Assignee: Eisai Co., Ltd., Tokyo, Japan

[22] Filed: Nov. 13, 1975

[21] Appl. No.: 631,603

[30] Foreign Application Priority Data
Nov. 13, 1974   Japan ............................ 49-130054

[52] U.S. Cl. ...................................... 195/2; 195/30
[51] Int. Cl.² ........................................... C12B 1/00
[58] Field of Search .................... 195/2, 30, 29, 49

[56] References Cited
UNITED STATES PATENTS

| | | | |
|---|---|---|---|
| 3,562,112 | 2/1971 | Gibian et al. | 195/49 X |
| 3,620,918 | 11/1971 | Moroe et al. | 195/2 |
| 3,635,795 | 1/1972 | Demain et al. | 195/2 |
| 3,841,966 | 11/1974 | Asai et al. | 195/2 |

*Primary Examiner*—Lionel M. Shapiro
*Attorney, Agent, or Firm*—Wenderoth, Lind & Ponack

[57] ABSTRACT

Novel process for biochemical optical resolution of 2DL-racemic compound of α-tocopherol ester or substances which contain the same, using culture broth, whole cell, or culture filtrate, which are obtained by cultivating microorganisms which possess an ability for hydrolysis of said ester. Beneficial advantage of the process resides in its low cost, simplicity and high resolution ratio.

16 Claims, No Drawings

PROCESS FOR BIOCHEMICAL OPTICAL RESOLUTION OF ALPHA-TOCOPHERAL

This invention relates to biochemical and optical resolution of dl-α-tocopherol or ester thereof. More particularly, this invention relates to a process for the separation of 2D or 2L isomer of α-tocopherol from the mixture of 2DL-racemic compound by a biochemical method.

α-Tocopherol is represented by the formula:

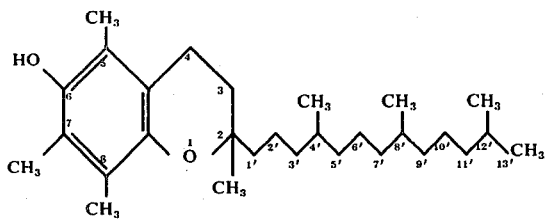

As shown in this formula, each of the carbon atoms at the positions 2, 4' and 8' is asymmetric. Therefore, there may exist eight different optical isomers of α-tocopherol.

When α-tocopherol is prepared by the condensation reaction of trimethyl hydroquinone with natural phytol, said α-tocopherol is a mixture of two diastereomers, i.e. 2D, 4'D, 8'D-α-tocopherol and 2, 4'D, 8'D-α-tocopherol. The mixture is hereinafter referred to as "2DL-α-tocopherol" in this specification and claims.

On the other hand, when α-tocopherol is prepared by the reaction of trimethyl hydroquinone with a synethesized racemic isophytol, the resulting α-tocopherol is a mixture of equal amounts of the aforementioned eight optical isomer. The latter mixture is also referred to as "2DL, 8'DL-α-tocopherol" in the specification and claims. When only the configuration at position 2 is referred to regardless of the configuration of side chains, said tocopherol is referred to 2DL-racemic compound, 2D-isomer or 2L-isomer, respectively.

α-Tocopherol and the ester thereof have Vitamin E activity, and the strength or ability is varied depending on the respective optical isomers. Refer to Journal of Association of Official Analytical Chemists, Vol. 55, No. 3, p.625 (1972), for example. According to the description of the reference, the strength of the natural substance or 2D, 4'D, 8'D-α-tocopherol acetate which is the same optical isomer as the natural substance is 1.36 IU/mg, while the strength of 2DL-α-tocopherol acetate is 1 IU/mg, and that of 2DL, 4'DL, 8'DL-α-tocopherol acetate is 1.0 IU/g. These values show that steric configuration of the side chain at the positions 4' and 8' does not essentially affect Vitamin E activity of α-tocopherol, but the strength depends mainly upon the steric configuration at position 2. Biological activity of 2DL-racemic compound has only about 73.5% as compared with that of 2D-isomer, independent of the steric configuration of the side chain at the positions 4' and 8' of side chain. These differences of the biological activity result from the fact that 2L-isomer exists in synthesized materials and the esters thereof.

α-Tocopherol and the ester thereof are broadly used as Vitamin E for human and veterinary medicines or as various additives for foods. Most of these α-tocopherol and esters thereof are produced and used as 2DL-racemic compound. However, the direct use, as pharmaceutical agent, of a racemic mixture containing non-natural type optical isomers, typically aminoacids, which are biologically non-active or low-active, has lately been questioned. Refer to Alience; "Molecular Pharmacology (Bunshi Yakurigaku)", translated into Japanese by M. Kimura and K. Takayanagi; Asakura Bookstore, Tokyo, Japan, p.61 (1967), for example.

The object of this invention is therefore to provide a process for the separation of α-tocopherol or the ester thereof which has been prepared by the condensation reaction of trimethylhydroquinone with natural phytol or racemic isophytol, into 2D-isomer and 2L-isomer.

There have been reported several processes to achieve such an object.

U.S. Pat. No. 2,215,398, for example, discloses the esterification methods by the use of optical active acids such as 3-bromo-d-camphor-sulfonic acid.

U.S. Pat. No. 3,153,053 mentions the method in which 2DL-α-tocopherol is converted to a complex salt with a piperazine compound, and then the resulting racemate is separated into individual isomers by the difference between their solubilities.

Furthermore, Japanese Pat. Pub. No. 12296/70 discloses the method in which several esters of 2DL-60-tocopherol are separated into individual isomers of their racemic compound by fractional crystallization. However, these known methods have some drawbacks.

In the case of U.S. Pat. No. 2,215,398, i.e. the method by active esterification, the optically active acids used as reagent for separation are usually expensive. In the cases of U.S. Pat. No. 3,153,053 and Japanese Pat. Pub. No. 12296/70, i.e. the method by the difference of solubilities and the method by fractional crystallization, the respective crystallization is not always selective. The dissolving and crystallizing procesures must therefore be repeated several times to provide desired optical purity. This requires complicated operations and undue time, and the yield is very low. Further, there is produced as by-product, a mixture of DL-compound having various DL-composite ratios for each time of crystallization, and treatment of said by-product is not always so easy. For example, Japanese Patent Publication No. 12296/70 discloses that when 102 g of 2DL-α-tocopherol acetate, the starting material, are subjected to fractional crystallization, there are obtained 8.9 g of the pure product which is identical with α-tocopherol acetate resulting from natural α-tocopherol. The yield of crystallization is however only 8.7%, and further there are 6 steps and about 28 days required for crystallization.

We have attempted to overcome these problems in the known methods, and found a biochemical method which effectively separates 2DL-α-tocopherol esters into the corresponding 2D-isomer and 2L-isomer.

This invention relates to a novel process which comprises using microorganisms which act on said racemic esters hydrolyze more selectively either 2L-isomer or 2D-isomer of said racemic compounds. This invention is a novel process for biochemical optical resolution, which entirely differs from the conventional chemical or physicochemical processes.

We have searched for microorganism having such optical resolution ability, and found that such ability exists in microorganisms such as *Candida sp.*, *Mucor sp.*, *Rhizopus sp.*, *Aspergillus sp.*, *Pseudomonas sp.* and the like. We accomplished the present invention, based on this discovery.

When search is made as to whether or not various microorganisms have such an ability for selective hydrolysis of tocopherol ester as mentioned above, the following method can be used, for example.

Aqueous solution containing 2% of 2DL-racemic ester of α-tocopherol for use as substrate and 0.2% of polyoxyethylenesorbitan-trioleate (Registered Trademark Tween 85) is subjected to ultrasonic wave treatment at 20 Kc to form an emulsion of the substrate.

Into a large test tube, 5 ml culture broth of the test microorganism are placed, and 5 ml of above-mentioned emulsion of substrate are added to the broth. After purging with nitrogen gas, the test tube is sealed hermetically and then shaken at 30° C for 24 hours to carry out an enzymatic reaction.

Subsequently, 10 ml of ethanol are added to said reaction solution to terminate the reaction. The solution is extracted twice with 10 ml quantities of petroleum ether. These petroleum ether extracts are combined and subjected to Emmerie-Engel's reaction to test for the detection of existence of free α-tocopherol. Refer to "Vitamine" Vol. 8, p.348 (1955).

Alternatively, the formation of the free α-tocopherol can be, as a convenient manner, detected by spotting said extract of petroleum ether on a thin layer plate carrying silica gel GF254, developing with benzene, spraying aqueous 40% sulfuric acid solution, and heating the plate.

Optical activities of the resulting free α-tocopherol and undecomposed α-tocopherol esters can be tested by the following method, for example.

Into one litre of reaction solution which was obtained in a similar manner as mentioned above, 800 ml of ethyl alcohol are added to terminate the reaction. The solution is then extracted four times with petroleum ether, in such manner that the extraction is made once with one liter of petroleum ether, and successively three times, each with 300 ml. The petroleum ether layers are combined, and the solvent contained therein is removed by vacuum distillation. The residues are dissolved in about 40 ml of benzene and subjected to silica gel chromatography using benzene as eluate. Fractions of free α-tocopherol and fractions of residual substrate, i.e. α-tocopherol ester, are fractionated respectively.

After removing benzene by vacuum distillation, the fraction of the free α-tocopherol is treated with potassium ferrocyanide according to the method of Donald R. Nelan et al. described in "Nature", Vol. 193, p.477 (1962), and the resulting oxidation product thereof is determined for the angle of optical rotation in isooctane. On the other hand, the fraction of the α-tocopherol ester is also determined for the angle of optical rotation, after the fraction is hydrolyzed with an alkali to convert to the free form, as follows:

As for the above-mentioned oily residue obtained by removing benzene, about 500 ml thereof are dissolved in 250 ml of ethanol. 250 Ml of 1% pyrogallol-ethanol solution are added to the solution. After heating to about 85° C, 50 ml of aqueous 50% KOH solution are immediately added thereto, and the reaction mixture is heated under reflux for 20 minutes, to hydrolyze the ester. The resulting free α-tocopherol was extracted with petroleum ether and treated with potassium ferrocyanide as mentioned above. The oxidation product is then determined for the angle of optical rotation. As to the values for specific rotatory power as a standard for calculation of an optical purity, reference is made to those disclosed in H. Mayer et al, Helvetica Chimica Acta, Vol. 46, p. 650, (1963). The specific rotary power of the oxidized product of 2D, 4'DL, 8'DL-α-tocopherol by the use of potassium ferrocyanide is +25.8, and that of 2D, 4'D, 8'DL-α-tocopherol is +24.9.

When the microorganisms used in the process of this invention are cultured, there may be used a culture medium which contains suitably nutrition sources used conventionally for culturing these microorganisms. i.e. carbon sources, nitrogen sources, inorganic salts, etc. There are used carbon sources such as D-glucose, starch and the other carbohydrates; nitrogen sources, such as peptone, ammonium sulfate and the other organic or inorganic nitrogen sources. Though the kinds of these nutrition sources and combination ratio thereof are varied depending upon the species of microorganisms employed, the suitable conditions for the object of this invention may be relatively easily determined by experimental procedure. In the case of *Candida cylindracea*, for example, there are effectively used the culture medium consisting of starch, soy bean powder and inorganic salts, as well as the synthesized medium consisting of kerosine, polyoxyethylene sorbitan mono-stearate (Registered Trademark, Tween 60) and inorganic salts.

Cultivation is wholly carried out aerobically. Therefore, shaking culture method or bubbling an agitating culture method may be used. Culture temperature is suitably within the range of from 25° to 32° C, and preferably within the range from 27° C to 30° C depending upon the species of the microorganisms. Suitable culture period is usually in the range of from 48 to 72 hours, though there may be cases where sufficient activities are provided in the period of 12 to 24 hours or less.

The resulting culture broths of the microorganisms are used for enzymatic reaction of this invention, in a form of broths per se; in a form of either whole cell or culture filtrate which are obtained after filtering the medium; or in a form of the treated products thereof. Such forms of the enzyme sources are suitably selected according to activity for the hydrolysis of tocopherol ester to be applied for the reaction, or the existing region of enzyme in culture broth or properties of the enzyme, and the selection depends upon the species of the microorganisms. For example, in the cases of *Aspergillus niger* and *Pseudomonas aeruginosa*, the culture filtrate is mainly used, while in the case of *Rhizopus oryzae*, the bacterium is mainly used. In the case of *Candida cylindracea*, the enzymatic activities are found in both the bacterium and the culture filtrate, but the culture filtrate is preferably used for the object of this invention. Examples of the products of the whole cell or the culture filtrate include the crude enzyme powder obtained by salting out the culture filrate with ammonium sulfate or by solvent-precipitation treatment with ethanol and the like; the concentrated liquid obtained by concentrating the culture filtrate, when the enzymatic activities are relatively stable to heat as in the activities of *Candida cylindracea* and *Pseudomonas aeruginosa;* the crude enzyme powder obtained by salting out or solvent precipitation of the concentrated liquid or the lyophilized powder of whole cells.

*Candida cylindracea* used in this invention is known as a microorganism for producing lipase. Refer to, e.g. Japanese Pat. No. 405384 and Journal of Japanese Agricultural Chemistry, Vol. 36, p. 858 (1962). There are also avilable in the market the enzyme preparations obtained from the culture filtrate of the above-mentioned microorganism under registered Trademark Lipase MY. This enzyme preparations on the market may also be used for the object of this invention.

As the esters of 2DL-racemic compound of α-tocopherol used as the substrate in this invention, there can be used any of the esters of straight or branched chain, unsubstituted or substituted with a halogen or carboxyl group, saturated or unsaturated aliphatic acid having 2 to 20 carbon atoms, such as acetic acid, monochloroacetic acid, propionic acid, butyric acid, isobutyric acid, valeric acid, isovaleric acid, caproic acid, caprylic acid, lauric acid, myristic acid, palmitic acid, stearic acid, linolic acid, succinic acid and the like. The esters of monochloroacetic acid and of stearic acid are most suitable. These substrates are added directly to the culture medium or the culture filtrate, or to the aqueous solution containing microorganism bodies or their various crude enzymes, such as M/15 phosphate buffer solution. Concentration of said substrate is preferably on the order of 1 – 100 mg/ml, particularly in the range of from 3 mg/ml to 15 mg/ml. The reaction is carried out by stirring sufficiently or in a form of an emulsion which has been prepared by adding about 0.5 mg/ml to 2.0 mg/ml of surfactant, such as polyoxyethylene nonylphenyl ether (registered Trademark Emulgen 905), because these substrates are generally insoluble in water.

The pH value in the reaction is generally in the range of pH 3 to pH 9, preferably in the range of pH 5 to pH 7, though it is varied depending upon the properties of the microorganisms or the enzymes produced by said microorganisms. The reaction is carried out by purging the space above the liquid in the reactor with nitrogen gas, allowing to stand, shaking or stirring the reaction mixture at the temperture ranging from 10° to 60° C, preferably from 25° to 35° C, for 0.5 to 60 hours.

The separation and purification of the free α-tocopherol and the unreacted α-tocopherol ester from the enzymatic reaction solution may be achieved by any conventional method for separation and purification, as follows: After the completion of the reaction, the reaction mixture is extracted with petroleum ether or benzene, the extracts are combined, and the solvent therein is removed by distillation under a reduced pressure. The residue is dissolved in a small amount of benzene or n-hexane, and subjected to silica gel chromatography according to a conventional method.

These above mentioned conditions of the cultivation, enzymatic reaction and purification are not always critical, but any suitable conditions can be selected depending upon the properties of the microorganisms or enzymes used for the reaction and also the substrate.

The preferable embodiments of this invention are illustrated by the following examples. But it is to be understood that these examples are for the purpose of illustration, and should not be construed as limiting this invention.

EXAMPLE 1

A 30 liter jar fermentor was charged with 12 liters of culture medium containing 10 ml of kerosin, 1 ml of polyoxyethylene sorbitane monostearate (Tween 60), 5 g of ammonium sulfate, 0.4 g of potassium dihydrogen phosphate, 0.2 g of magnesium sulfate, 0.03 g of ferrous sulfate and 0.01 g of manganese sulfate per liter of the culture medium (hereinafter referred to KT medium). Said mixture was heated at 120° C for 10 minutes to sterilize it.

On the other hand, said KT medium was inoculated 3 with liters of culture seeds of Candida cylindracea ATOC 14830 which had been cultured for 24 hours in a culture medium containing 10 g of glucose, 5 g of peptone, 3 g of the yeast extract, and 3 g of the malt extract per liter of the medium (hereinafter referred to MY medium). The cultivation was achieved under the conditions as follows:

| | |
|---|---|
| Culture time | 48 hours |
| Culture temperature | 27° C |
| Volume of aeration | 30 liters/min. |
| Revolution of stirring | 300 r.p.m. |

After the cultivation was over, the microorganism was filtered and removed to provide 15 liters of culture filtrate which was then concentrated to 750 ml at the bath temperature of 40° C. Said concentrated solution was used as the crude enzyme solution in enzymatic reaction for optical resolution of 2DL-racemic compound.

Thus, a one liter glass reactor was charged with 800 ml of the substrate suspension containing 5.6 g of 2DL, 4'DL, 8'DL-α-tocopherol stearate, and 200 ml of said crude enzyme solution were added to said suspension. After purging with nitrogen gas, the reactor was sealed, and stirred at 30° C for 48 hours, and then 800 ml of ethanol were added to terminate the reaction. The resulting mixed solution was extracted once with 900 ml of petroleum ether and thrice with 350 ml quantities of the same solvent. A total of 2170 ml of the petroleum ether layers was combined, and the amount of α-tocopherol therein was determined. The content of about 23 g of the free α-tocopherol was confirmed, which corresponds to a hydrolysis ratio of 66.4%.

The extract was concentrated and evaporated to dryness, and the residue was dissolved in 40 ml of benzene. Said benzene solution was charged on the column filled with 270 g of silica gel therein, and subjected to column chromatography by using benzene as developing fluid. The extract was fractionated into fractions of 19 ml each. It was found that unreacted substrate, α-tocopherol stearate, was extracted in the fraction Nos. 27 to 38.

These fraction Nos. 27 to 38 were combined together, and then concentrated and evaporated to dryness, and 1.9 g of waxy residue were obtained. This product exhibited a single spot on thin layer chromatograph, and this spot was identified with that of α-tocopherol stearate. After hydrolyzing said product by an alkali, it was subjected to the potassium ferrocyanide treatment and determined for the angle of optical rotation. The specific rotation was +21.98. It was found that product was 2D, 4'DL, 8'DL- α-tocopherol stearate having about 93% of optical purity.

On the other hand, the fraction Nos. 52 to 84 were combined together, and then concentrated and evaporated to dryness, to obtain about 2.6 g of an oily residue which is identical with the free α-tocopherol. When said oily product was subjected to the potassium ferrocyanide treatment, the specific rotation of the resulting solution was −11.04. As the result of this determination, it was found that the oily product was a mixture of 2D and 2L isomers in the ratio of 28.5 : 71.5.

EXAMPLE 2

To 2.5 liters of crude enzyme solution obtained by the same procedure as in Example 1, 7.5 liters of cold ethanol were added, and the mixture was stirred for 30 minutes under cooling with ice. The resulting precipitates were removed by filtration, and the filtrate was dried in vacuo in the presence of phosphorous pentoxide, to obtain 265 g of crude enzyme powder.

On the other hand, a 500 ml flask was charged with 2 g of 2DL, 4'D, 8'D-α-tocopherol stearate, 200 ml of M/15 phosphate buffer solution (pH 7.0) and 200 mg of polyoxyethylene nonylphenyl ether. The mixture was heated to about 60° C and vigorously shaked to produce an emulsion, and then cooled to room temperature.

4.2 G of said crude enzyme powder were dissolved in 100 ml of the same phosphate buffer solution to obtain a crude enzyme solution, which is then added to the emulsion, purged with nitrogen gas, and sealed in the flask hermetically. The enzymatic reaction was carried out at 30° C for 24 hours while rotating and shaking the flask.

After the reaction was over, the extraction with petroleum ether and chromatography with silica gel were effected as in Example 1. From the fraction Nos. 33 to 39, there were obtained 0.8 g of unreacted substrate, and from fraction Nos. 53 to 72, there were obtained 0.8 g of product by hydrolysis.

| | |
|---|---|
| Ratio of hydrolysis | 61% |
| Unreacted substrate | $[\alpha]_D = +18.78$ |
| | (C = 1.0) |
| Optical purity of | |
| 2D, 4'D, 8'D-α-tocopherol | |
| stearate | 86.4% |
| Product by hydrolysis | $[\alpha]_D = -11.53$ |
| | (C = 1.0) |
| Composite ratio of | |
| 2D form : 2L form | |
| α-tocopherol | 27.5 : 72.5 |

EXAMPLE 3

6 G. of 2DL, 4'DL, 8'DL-α-tocopherol linolate were suspended in 250 ml of M/5 phosphate buffer solution, and then 2 g of Lipase - MY (Trademark of Meito Sangyo Co., Ltd. in Japan) were added to the suspension. The vessel was purged with nitrogen gas, and stirred at 30° C. for 12 hours.

After the completion of the reaction, procedures of extraction with petroleum ether and silica-gel chromatography were carried out in the same manner as in Example 1. Ratio of hydrolysis of the product is about 7.7%. There were obtained 0.3 g of an oily substance, which is indentical with the free α-tocopherol, from the chromatogram fraction Nos. 28 – 41. Since the product showed the specific rotation of −15.0, it is confirmed that the product is 2L, 4'DL, 8'DL-α-tocopherol having an optical purity of 79%.

EXAMPLE 4

2.5 G. of 2DL, 4'DL, 8'DL-α-tocopherol caproate were charged to a flask having 500 ml capacity. There were then added, to the said caproate, 200 ml of M/15 phosphate buffer solution (pH 7.0) and 50 ml of crude enzyme solution which was prepared in an almost similar manner as in Example 1. The flask was purged with nitrogen gas and sealed. Fermentation reaction was effected by stirring under revolution at 30° C. for 24 hours.

After the reaction was completed, there were added 200 ml of ethanol to the reaction mixture, which was then extracted once with 250 ml of peteroleum ether and further four times with 100 ml quantitites of petroleum ether, respectively. It was confirmed by Emmerie-Engel reaction that the resulting extract contains 310 mg of the free α-tocopherol. Ratio of hydrolysis amounted to 15.2%.

The extract solution was concentrated and evaporated to dryness. The resulting residue was dissolved in about 25 ml of benzene. The solution was applied to a column which was previously filled with 140 g of silica gel. Column chromatography procedure was effected in the same manner as in Example 1. The fraction Nos. 33 – 37 were collected, and the solvent was distilled off from the fractions. There were obtained about 270 mg of an oily residue which was identical with the free α-tocopherol. Since the oily substance has a value $[\alpha]_D = -21.7°$ (C = 0.83), it was shown that the substance is 2L, 4'DL, 8'DL-α-tocopherol of about 92% optical purity.

The corresponding unreacted caproate was recovered from the fraction Nos. 19 – 25. Since the value of the specific rotation is +7.97, the calculated optical purity of 2D, 4'DL, 8'DL-α-tocopherol caproate is about 65%.

EXAMPLE 5

Fermentation reaction and extract-purification procedure were repeated under the same conditions as in Example 4, except that the caproate as substrate in Example 4 was substituted by the corresponding succinate. Ratio of hydrolysis of the resulting product was 20.8. When the product was subjected to silica-gel chromatography, there was obtained, from the fraction Nos. 32 – 36, 2L, 4'DL, 8'DL-α-tocopherol having about 86% optical purity in a form of an oily substance.

EXAMPLE 6

500 Ml of Bouillon culture medium were charged to a Sakaguchi flask having a 2 liters capacity. *Pseudomonas aeruginosa* IFO 3453 strain was inoculated to the culture, and the whole was cultivated by shaking at 30° C. for 3 days. When the cultivation has been completed, pH value of the culture broth showed 8.20. The culture broth was centrifuged. To the supernatant, there were added 5 g of 2DL, 4'DL, 8'DL-α-tocopherol monochloracetate, 500 mg of polyoxyethylene nonylphenyl ether and 500 ml of M/15 phosphate buffer solution (pH 7.0). The vessel was purged with nitrogen gas, and the contents were stirred at 30° C. for 48 hours.

After the completion of the reaction, procedures of extraction and chromatography for purification were carried out in accordance with the conventional manner, to form 1.7 g of the free α-tocopherol.

| | |
|---|---|
| Ratio of hydrolysis: | 30% |
| Product by hydrolysis: | $[\alpha]_D = +9.0$ |
| | (C = 1.06) |
| Optical purity of | |
| 2D-α-tocopherol: | 67.4% |

From the above data, it was confirmed that *C. cylindracea* ATCC 14830 hydrolyzes mainly the ester of the 2L-iosmer, while Ps. aeruginosa acts mainly to hydrolyze the ester of the 2D-isomer.

EXAMPLE 7

400 Ml of Ym culture medium were charged to a flask having a capacity of 2 liters. Rhizopus oryzae IFO 4744 strain was inoculated to the culture medium, and the whole was cultivated by reciprocal shaking. To the culture broth, there were added kerosin and polyoxyethylene sorbitan monostearate (Tween 60), so as to make the concentration of kerosin 1% (v/v) and that of polyoxyethylene solbitan monostearate 0.1% (w/v). Cultivation was continued for additional 24 hours. After completion of the cultivation, the resulting culture medium was filtered under suction to collect mycelium. There were thus obtained 40 g of wet mycelium.

There were charged, to a 1 litre flask, 5 g of 2DL, 4'DL, 8'DL-α-tocopherol monochloroacetate, 0.6 g of polyoxyethylene nonylphenyl ether and 500 ml of M/15 phosphate buffer solution (pH 7.0).

To the substrate solution, there were suspended 40 g of the above-mentioned wet mycelium.

The vessel was purged with nitrogen gas, and the contents were subjected to reaction by rotary shaking at 30° C. for 48 hours. After the completion of the reaction, procedures of extraction with petroleum ether and silica gel chromatography were carried out in accordance with the conventional manner. There were thus obtained 0.7 g of an oily substance which is identical with the free α-tocopherol.

| | |
|---|---|
| Ratio of hydrolysis: | 16.5% |
| Product by hydrolysis: | $[\alpha]_D^{20} = +5.78$ |
| | (C = 0.78) |
| Optical purity of 2D-α-tocopherol: | 61.2% |

EXAMPLE 8

400 Ml of YM culture medium were charged to a 2 liter flask. Aspergillus niger IFO 4043 train was inoculated to the culture medium, and the whole was stirred an cultivated at 27° C. for 72 hours. After the completion of the cultivation, the mycelium were removed by filtration with suction. 700 Ml of culture filtrate were obtained from two lots of the 2 liter flask.

To the culture filtrate, there was added 10 g of 2DL, 4'DL, 8'DL-α-tocopherol monochloroacetic acid ester, 1 g of polyoxyethylene nonylphenyl ether and 300 ml of M/15 phosphate buffer solution (pH 7.0). The whole was charged to a 2 liter flask which is then purged with nitrogen gas, after which the flask was stirred at 30° C. for 2 days. After the reaction has been completed, procedures of extraction with petroleum ether and silica-gel chrometography were carried out in accordance with the conventional manner. There were thus obtained 0.8 g of an oily substance which is identical with tocopherol ester as substrate.

| | |
|---|---|
| Ratio of hydrolysis: | 92.7% |
| Unreacted substrate: | $[\alpha]_D = +16.0$ |
| | (C = 1.31) |
| Optical purity of 2D, 4'DL, 8'DL-α-tocopherol monochloroacetate: | 81.0% |

EXAMPLE 9

5 G of 2DL, 4'DL, 8'DL-α-tocopherol stearate, 500 mg of polyoxyethylene nonylphenyl ether, and 125 ml of distilled water were charged to a 500 ml flask. The whole was heated to about 60° C, and shaken vigorously to form an emulsion, and then cooled to room temperature. After charging the crude enzyme solution, which was prepared by dissolving 5 g of Lipase MY into 125 ml of M/15 phosphate buffer solution (pH 7.0), the flask was purged with nitrogen gas and sealed. The enzymatic reaction was carried out at 30° C for 24 hours under rotary shaking.

After the completion of the reaction, procedures of extraction with petroleum ether, and silica gel chromatography were carried out in the same manner as in Example 1. Ratio of hydrolysis was about 71%. From the fraction Nos. 29 to 39 of the chromatography, 1.53 g of unreacted substrate were obtained, while 1.40 g of the products by hydrolysis were obtained from the fraction Nos. 55 to 81.

| | |
|---|---|
| Unreacted substrate: | $[\alpha]_D = +22.65$ |
| | (C = 1.15) |
| Optical purity of 2D, 4'DL, 8'DL-α-tocopherol stearate: | 93.9% |
| Products by hydrolysis: | $[\alpha]_D = -9.28$ |
| | (C = 1.15) |
| Composite ratio of 2D form : 2L form α-tocopherol: | 32 : 68 |

What is claimed is:

1. A process for biochemical optical resolution of a 2DL-racemic compound of an α-tocopherol ester or substance containing said racemic ester, which comprises mixing said racemic ester or said substance with culture broth, whole cells, culture filtrate or an enzyme product thereof, obtained by cultivating a Candida sp., Mucor sp., Rhizopus sp., Aspergillus sp. or Pseudomonas sp. microorganism which acts on said racemic ester to more selectively hydrolyze the 2D-isomer or the 2L-isomer of said racemic ester, to obtain α-tocopherol or an ester thereof having a predominant proportion of either the 2D-isomer or the 2L-isomer.

2. The process according to claim 1, wherein the 2DL-α-tocopherol ester is the ester of an aliphatic carboxylic acid having 2 to 20 carbon atoms.

3. The process according to claim 2, wherein the aliphatic carboxylic acid is selected from the group consisting of acetic acid, monochloroacetic acid, propionic acid, butyric acid, isobutyric acid, valeric acid, isovaleric acid, caproic acid, caprylic acid, lauric acid, myristic acid, palmitic acid, stearic acid, linolic acid and succinic acid.

4. The process according to claim 2, wherein the aliphatic carboxylic acid is monochloroacetic acid.

5. The process according to claim 2, wherein the aliphatic carboxylic acid is stearic acid.

6. The process according to claim 1, wherein the microorganism is selected from Candida sp.

7. The process according to claim 1, wherein the microorganism is selected from Mucor sp.

8. The process according to claim 1, wherein the microorganism is selected from Rhizopus sp.

9. The process according to claim 1, wherein the microorganism is selected from Aspergillus sp.

10. The process according to claim 1, wherein the microorganism is selected from *Pseudomonas sp.*

11. The process according to claim 1, wherein the culture broth is used.

12. The process according to claim 1, wherein the whole cells are used.

13. The process according to claim 1, wherein the culture filtrate is used.

14. The process according to claim 1, wherein the enzyme product of the culture broth, whole cells or culture filtrate is used.

15. The process according to claim 14, wherein the enzyme product is crude enzyme powder.

16. The process according to claim 14, wherein enzyme product is concentrated liquid obtained by concentrating the culture filtrate.

* * * * *